US00PP14084P29

(12) United States Plant Patent
Utecht

(10) Patent No.: US PP14,084 P2
(45) Date of Patent: Aug. 19, 2003

(54) GERANIUM PLANT NAMED 'FIP 749'

(75) Inventor: Angelika Utecht, Montabaur (DE)

(73) Assignee: Florfis AG, Binnengen (CH)

( * ) Notice: Subject to any disclaimer, the term of this patent is extended or adjusted under 35 U.S.C. 154(b) by 0 days.

(21) Appl. No.: 10/259,593

(22) Filed: Sep. 30, 2002

(51) Int. Cl.[7] ..... A01H 5/00
(52) U.S. Cl. ..... Plt./329

(58) Field of Search ..... Plt./329

*Primary Examiner*—Kent Bell
(74) *Attorney, Agent, or Firm*—Foley & Lardner

(57) ABSTRACT

A new and distinct cultivar of geranium plant named 'Fip 749' characterized by the combined features of lavender-rose, semi-double flowers, numerous, medium sized umbels, dark-red peduncles, dark-green foliage mostly without zonation, compact and tight, well-branched plant habit, and relatively early flowering.

1 Drawing Sheet

Latin name of the genus and species of the plant claimed: *Pelargonium zonale L'Heritier.*
Variety denomination: 'Fip 749'.

BACKGROUND OF THE INVENTION

The present invention comprises a new and distinct cultivar of geranium, botanically known as *Pelargonium zonale,* and hereinafter referred to by the cultivar name 'Fip 749'.

'Fip 749' is a product of a planned breeding program which had the objective of creating new zonal geranium cultivars with violet to lavender flower color in combination with dark-green foliage.

'Fip 749' originated from a hybridization made by the inventor Angelika Utecht in a controlled breeding program in Galdar, Gran Canaria, Spain, in 1997. The female parent was an unpatented hybrid seedling, no. 95-104-9, having deep purple-pink, single-type flowers, dark-green foliage, and relatively compact plant habit. The male parent of 'Fip 749' was the commercial variety 'Arlena', (Plant Breeder's Rights grant under the denomination 'Penarl'), with light lavender, semi-double flowers, medium to light green foliage without zonation, and small, compact plant habit.

'Fip 749' was selected as one flowering plant within the progeny of the stated cross by Angelika Utecht in 1998 in a controlled environment in Galdar, Gran Canaria, Spain. The first act of asexual reproduction of 'Fip 749' was accomplished when vegetative cuttings were taken from the initial selection in the fall of 1998 in a controlled environment in Galdar, Gran Canaria, Spain, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fip 749' are firmly fixed and are retained through successive generations of asexual reproduction.

'Fip 749' has not been observed under all possible environmental conditions. The phenotype may vary significantly with variations in environment such as temperature, light intensity and day length.

The following observations, measurements, and comparisons describe plants grown in Hillscheid, Germany, under greenhouse conditions which approximate those generally used in commercial practice.

BRIEF SUMMARY OF THE INVENTION

The following traits have been repeatedly observed and are determined to be basic characteristics of 'Fip 749' in combination distinguish this geranium as a new and distinct cultivar:

1. Lavender-pink and white, semi-double flowers;
2. numerous medium sized inflorescences on reddish peduncles;
3. dark green foliage without or with only very weak zonation on young leaves,
4. compact, and relatively low, rounded plant habit; and
5. early spring flowering response for a variety with dark-green foliage.

Of the many commercial cultivars known to the present inventor, the most similar in comparison to 'Fip 749' are the patented variety 'Fislypso' (U.S. Plant Pat. No. 11,162), and the variety 'Fip 765' (Co-pending U.S. Plant patent application No. 10/259,584).

In comparison to 'Fislypso', 'Fip 749' has a slightly deeper and more pink tone of flower color, more distinct white zones at the bases of the upper petals, shorter peduncles and dark-green, instead of medium-green, foliage.

In comparison to 'Fip 765','Fip 749' has a more rose, less violet hue of main flower color, roughly similar plant habit and size, but somewhat shorter peduncles.

BRIEF DESCRIPTION OF THE DRAWING

The accompanying photographic drawing shows typical flower and foliage characteristics of 'Fip 749' with colors being as true as possible with an illustration of this type. The drawing depicts a side elevational view of a typical flowering potted plant of 'Fip 749'.

DETAILED DESCRIPTION OF THE INVENTION

The measurements were taken in Hillscheid, Germany, in mid May 2002, 10 weeks after planting of rooted cuttings. The plants were growing in 14 cm plastic pots, they had not been pinched. In the following description color references are made to The Royal Horticultural Society Colour Chart. The color values were determined indoors from plants developed in a green-house in May 2002 in Hillscheid, Germany.

Inflorescence:

Umbel:

*Shape.*—Intermediate between umbrella and semi-spherical shape.

*Average diameter.*—98 mm.

*Average depth.*—50 mm.

*Peduncle length.*—145 mm.

*Peduncle color.*—Mainly reddish brown, RHS 183 B, green near base, RHS 143 B.

*Pedicel length.*—25 mm, no spur.

*Pedicel color.*—Reddish brown, RHS 181 A.

*Number of flowers per umbel.*—About 20–25.

Corolla:

*Average diameter.*—52 mm.

*Form.*—Semi-double.

*Shape.*—Round outline, flat cup shape.

*Number of petals.*—7–9.

*Number of petaloids.*—0–1.

*Shape of petals.*—Obovate, base acute, upper end rounded, margin entire.

*Size of petals.*—Upper petals: 30 mm long, 22–23 mm wide lower petals: 24–26 mm long, 22–24 mm wide.

*Color (general tonality from a distance of three meters).*—Lavender-pink.

*Color of upper petals.*—Main part RHS 68 A, near base white, RHS 155 A.

*Markings of upper petals.*—Two weak pink veins, RHS 68 C.

*Color of lower petals.*—Approximately RHS 74 C.

*Markings of lower petals.*—None.

*Color of lower surface of petals.*—Mainly RHS 78 D, middle, lighter RHS 75 C.

*Petaloids.*—Same color as petals.

*Color of sepals.*—Outer surface: green, RHS 143 B, base RHS 179 A: inner surface: green, RHS 143 C, base RHS 179 B.

*Number of sepals.*—5.

*Shape of sepals.*—Linear to lanceolate, acute tip, truncate base, surface with very weak pubescence, margin entire.

*Size of sepals.*—12–13 mm long, 3–4 mm wide for the largest upper sepal, 2 mm in width for the other sepals.

Bud: (just prior to petals unfolding).

*Shape.*—Elliptical.

*Color of sepals.*—Green, RHS 143 A, base RHS 179 A.

*Color of petals.*—RHS 72 D near margin, marbled with lighter spots: RHS 73C to 73D.

*Length.*—21 mm.

*Width.*—12 mm.

Reproductive organs:

*Androecium.*—5–7, occasionally 9 fertile anthers, moderate pollen, orange, RHS 30 A, filaments white, RHS 155 D, to light-pink, RHS 68 C.

*Gynoecium.*—One pistil, style and stigma pink, RHS 66 D, stigma 5–6-lobed.

*Fertility/seed set.*—No seed set observed.

Spring flowering response period: In Hillscheid, Germany, in 2002 plants had on average 0.8 flowers opened 8 weeks after planting of rooted cuttings.

Outdoor flower production: Continuously and rich flowering, the flower count in 2002 in Hillscheid, Germany, indicated about 5 inflorescence per plant in mid May.

Durability: Good stability of flower color, fair rain resistance.

Lastingness of the individual flower: About 6 days at 18° C., about 15 days for the umbel.

Fragrance: None.

PLANT

Foliage:

*Shape.*—Kidney-shaped with weak lobes, cordate base, with the gap between the lowest lobes almost closed.

*Margin.*—Distinctly bi-crenate, somewhat wavy.

*Texture.*—Upper surface smooth, velvety, dull to slightly glossy.

*Size of leaf.*—90 mm wide, 51 mm long.

*Color of upper surface.*—Dark green, approximately RHS 137 A to RHS 137 B.

*Color of zonation.*—Deeper green, between RHS 137 A and RHS 147 A.

*Color of lower surface.*—RHS 137 D.

*Petioles.*—70–90 mm long, about 3 mm diameter, light green in color, approximately RHS 143 C.

General appearance and form:

*Stem color.*—Green, RHS 143 A.

*Internode length.*—10–15 mm.

*Branching pattern.*—6.3 branches.

*Plant size.*—Height 19.6 cm (10-week-old plants, as described); width 28.4 cm as measured from the top of the soil (base of the main stem) to the surface of the foliage canopy without inflorescences.

Pest/disease resistance/susceptibility: No observations to date.

I claim:

1. A new and distinct cultivar of geranium plant named 'Fip 749', as described and illustrated herein.

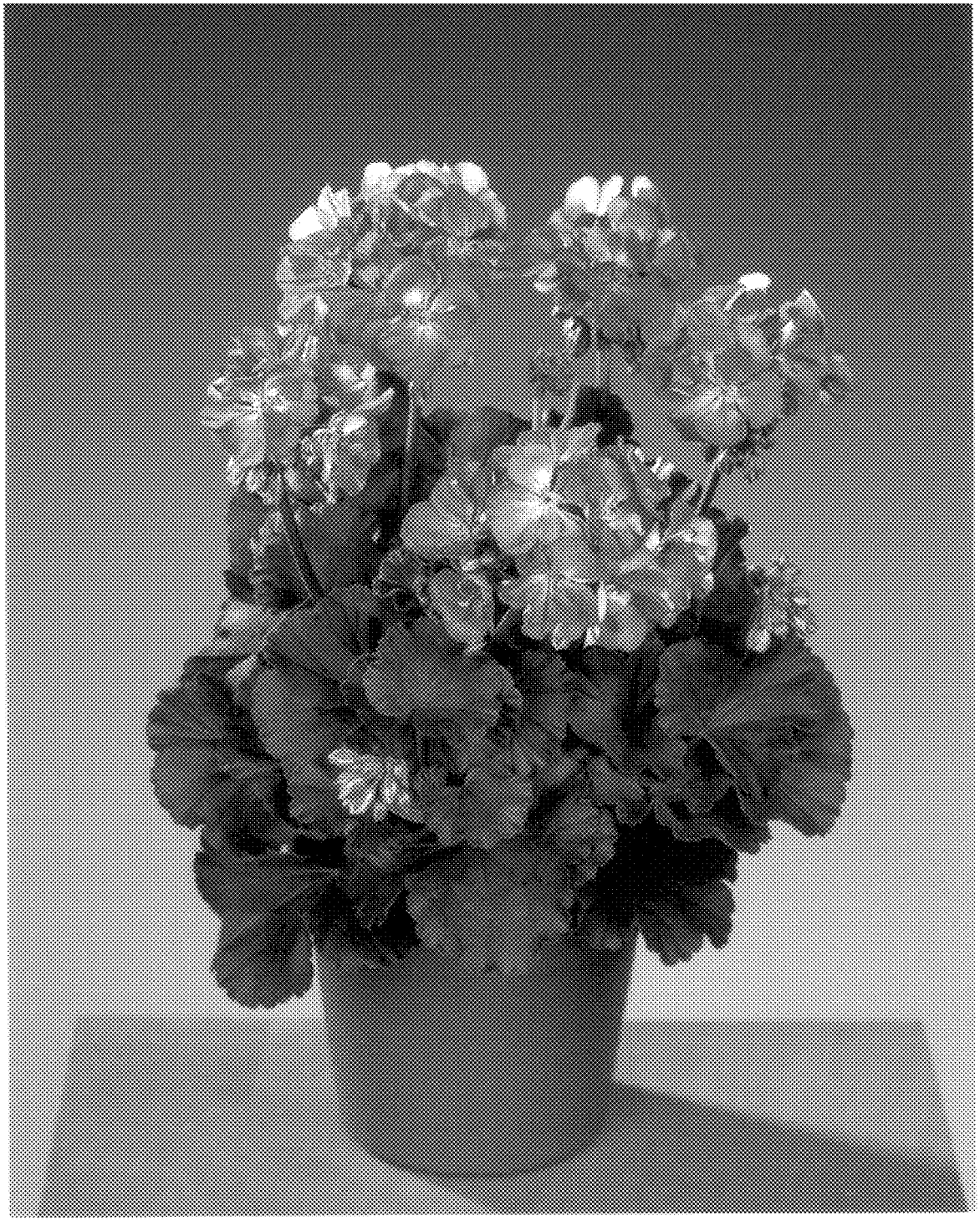

* * * * *